United States Patent [19]
Al-Dahir

[11] Patent Number: 5,846,544
[45] Date of Patent: Dec. 8, 1998

[54] COMPOSITION AND METHOD FOR REDUCING BLOOD SUGAR LEVELS IN DIABETIC HUMANS

[76] Inventor: Holly Christine Al-Dahir, 4521 Conlin St., Metairie, La. 70006

[21] Appl. No.: 891,590

[22] Filed: Jul. 11, 1997

[51] Int. Cl.⁶ ..................................................... A61K 35/78
[52] U.S. Cl. ....................... 424/195.1; 514/783; 514/866; 514/884
[58] Field of Search .......................... 424/195.1; 514/783, 514/866, 884

[56] References Cited

U.S. PATENT DOCUMENTS

| | | | |
|---|---|---|---|
| 308,050 | 11/1884 | Bevier | 424/195.1 |
| 1,627,963 | 5/1927 | Fuller | 424/195.1 |
| 5,162,037 | 11/1992 | Whitson-Fischman | 600/12 |
| 5,536,506 | 7/1996 | Majeed et al. | 424/464 |
| 5,578,338 | 11/1996 | Shimabukuro | 426/597 |

OTHER PUBLICATIONS

Heinerman, J.; *Encyclopedia of Healing Herbs and Spices*, Prentice Hall, Englewood Cliffs, N.J., 1996, pp. 61, 62, 458, 459.

*Primary Examiner*—Francisco C. Prats
*Attorney, Agent, or Firm*—Michael D. Carbo

[57] ABSTRACT

The present invention concerns a method and composition for reducing blood sugar levels in diabetic human subjects. Practice of the invention requires ingestion of bilberry fruit and valerian root in timed relation to meals. Neither bilberry fruit nor valerian root alone achieve the lowering and regulation of blood sugar levels achieved by the combination. Practice of the invention requires ingestion of bilberry fruit with valerian root.

4 Claims, No Drawings

COMPOSITION AND METHOD FOR REDUCING BLOOD SUGAR LEVELS IN DIABETIC HUMANS

BACKGROUND OF THE INVENTION

The present invention relates to the lowering and regulation of glucose levels in diabetic humans, and more particularly to the lowering and regulation of blood sugar levels in diabetic humans through the ingestion of valerian root and bilberry fruit preparations and extracts.

Before the advent of insulin, diabetes and hypoglycemia were treated with plant medicines. In 1980, the World Health Organization urged researchers to examine whether traditional medicines possessed any real effects. In the last twenty years scientific investigation has confirmed the efficacy of many of these preparations. Valerian root (valeriana officianalis) has not been previously known, either alone or in combination with other plant components, to be effective in lowering or otherwise regulating glucose levels in diabetic subjects.

Bilberry (vaccinlium myrtillus), or European blueberry, is a shrubby perennial that grows in the woods and forest meadows of Europe. The fruit is a blue-black berry that differs from an American blueberry in that its meat is also blue-black. Bilberry-leaf tea has a long history as a folk treatment for diabetes. This use is supported by research which has shown that oral administration reduces hyperglycemia in normal and diabetic dogs, even when glucose is injected intravenously at the same time. Allen, F. M., "Blueberry Leaf Extract: Physiologic and Clinical Properties in Relation to Carbohydrate Metabolism." Journal of the American Medical Association 89: 1577–81, 1927. Beaver, B. and Zahand, G.: "Plants With Oral Hyperglycemic Action." Quarterly Journal of Crude Drug Research, 17: 139–96, 1979. It has been thought that the berries or extracts of the berries offer even greater benefit then the tea. Michael T. Murray, *Diabetes and Hypoglycemia* (Prima Publishing, 1994).

Oral ingestion of bilberry fruit by diabetic subjects who are maintaining a diabetic diet is not known to regulate glucose levels in the blood. However, oral ingestion of bilberry fruit in combination with valerian root in timed relation with ingestion of meals of a diabetic diet has been discovered to provide lowering and regulation of glucose levels in diabetic subjects. The invention provides for a method for reducing blood sugar levels in diabetic humans by the ingestion of valerian root and bilberry fruit in diabetic human subjects who are also maintaining a diabetic diet such as that of the American Diabetes Association.

SUMMARY OF THE INVENTION

The present invention concerns a method and composition for reducing blood sugar levels in diabetic human subjects. Practice of the invention requires ingestion of bilberry fruit and valerian root in timed relation to meals. Neither bilberry fruit nor valerian root alone achieve the lowering and regulation of blood sugar levels achieved by the combination. Practice of the invention requires ingestion of bilberry fruit with valerian root.

DETAILED DESCRIPTION OF THE INVENTION

The efficacy of oral ingestion of bilberry fruit and valerian root on the lowering and regulation of blood sugar levels of diabetic humans was determined through the following examples.

EXAMPLE 1

A Caucasian male, 12 years of age, approximately 112 pounds and 5'1" inches tall, having Type I (insulin insufficient) diabetes mellitus since five and one half years of age, being maintained on an insulin dosage 32 NPH in a.m. and 18 NPH in p.m., plus a sliding scale regular (one half cc per kilogram of body weight per day), taking no vitamin or mineral supplements, being active although not on a regular exercise schedule, and being maintained on a diabetic diet (American Diabetes Association diet), had blood glucose levels between 200 mg/dl and 450 mg/dl daily, experienced polyuria, hyperglycemia, glycosuria, poor height gain, poor weight gain, generally poor health and constant hunger.

An initial dose of 40 milligrams of bilberry fruit (in the form of extract capsules from Sundown Herbal, Boca Raton, Fla.) and 400 milligrams of valerian root (milled herbs in capsules from Sundown Herbal) were orally ingested approximately thirty minutes after breakfast. After a mid-morning snack, a mid-day blood sugar reading was 30 mg/dl. Orange juice was provided to increase blood sugar level. Thereafter, daily doses (three times per day) were administered for approximately six months, comprising one dose taken thirty minutes after each meal. One dose before bedtime was added 5½ months after the initial dose in order to lower morning blood glucose level. The human subject is now generally hypoglycemic (below 70 mg/dl), running between 45 and 160 mg/dl in the morning, mostly below 70 mg/dl. The reading before dinner runs between 65 and 259 mg/dl, the higher figure showing a possible rebound reaction. The before bedtime reading was between 42 and 89 mg/dl. The subject has reduced glycosuria and has no polyuria. The subject has no symptoms of hyperglycemia even though the blood sugar reading is sometimes in excess of 200 mg/dl. The subject has no symptoms of hypoglycemia, except hunger, even though the blood sugar levels are often below 70 mg/dl. When the subject misses a dose of the bilberry fruit extract and the valerian root, blood sugar level rises to between 200 and 400 mg/dl.

Before treatment with the bilberry fruit and valerian root, this subject's glycosylated hemoglobin level was 12. Glycosylated hemoglobin levels were reduced during treatment to 10.2 after one month, and 9.3 after three months.

EXAMPLE 2

A forty year old African American male subject weighing 240 pounds and being 6'4" in height, having a history of diabetes from the distaff side, diagnosed with Type II (insulin resistance) for four years, was being maintained on an insulin dosage of seven regular, twenty-eight NPH in the a.m., twenty-one NPH in the p.m., and maintained on a diabetic diet, had blood sugar levels of 225 mg/dl in the a.m. and 83 mg/dl in the p.m., had hyperglycemic symptoms of polyuria, thirst and hunger, blood pressure of 180/90, controlled with medication, and on a diabetic diet.

An initial dosage of bilberry fruit and valerian root were administered three times per day approximately thirty to forty-five minutes after each meal for about five months. The dosage was a single 375 mg bilberry fruit capsule (Herbal Harvest, Inc., Bohemia, N.Y. 11716) containing the milled herb and one 450 mg valerian root capsule (Herbal Harvest, Inc.) containing the milled herb. The initial dose caused a 60 point drop (from 200 mg/dl to 140 mg/dl in blood sugar). The subject started exercising one half hour daily and refrained from snacks between meals. The bilberry fruit and valerian root were ingested three times per day for approximately five months.

After regular doses of the herbs, insulin requirements were reduced to three regular, 10 NPH in the a.m., 13 NPH in the p.m., with no insulin at night on weekends. Morning blood glucose was approximately 112 mg/dl, while p.m. blood glucose was approximately 93 mg/dl. Blood pressure was 165/89 without medication. The subject no longer had polyuria, excessive thirst, hyperglycemia or hypoglycemia.

EXAMPLE 3

A fifty-five year old Caucasian male weighing 335 pounds and standing 5'6" tall had Type II non-insulin dependent diabetes mellitus for four years, being maintained on a sulfonylulurea hypoglycemic agent, specifically chlorpropamide, as well as being maintained on a blood pressure medication and a weight controlled medication, and not on a diabetic diet and not exercising, maintained blood sugar between 300 and 400 mg/dl (300 mg/dl in the a.m.). The subject experienced hyperglycemia symptoms and was very hyperglycemic.

Subject orally ingested 375 milligrams of bilberry fruit Herbal Harvest, Inc.) and 530 milligrams of valerian root Nature's Resource Products, Michigan Hills, Calif.) after each meal, plus a double dose in the evening. Subject also went on to a diabetic diet, began to exercise one half hour per day, and ceased eating between meals.

On the initial dose, blood sugar levels dropped 40 mg/dl, then dropped 20 mg/dl per day until blood sugar level reached 200 mg/dl. Subject took the indicated dosage for one month.

It is noted that, beginning one month before initial dosage of the herbs, subject took vanadyl sulfate (5,000 mcg) chromium picolinate (250 mcg), and a multi-vitamin capsule once daily with a meal, with no effect on blood sugar level. Vanadyl sulfate and chromium picolinate are know hypoglycemic agents. When subject's blood sugar level was reduced to approximately 200 mg/dl, subject began exercising. The effects on the subject were that glucose blood levels were reduced to between 150 and 160 mg/dl in the a.m. and to 110 mg/dl in the p.m. After six weeks, a.m. blood sugar levels were reduced to 130 mg/dl.

It is emphasized that the ingestion of the combination of valerian root and bilberry fruit does not work as well if that combination is not ingested within 30 to 45 minutes after each meal of a diabetic diet. The subject in example 3 went off a diabetic diet for six weeks. Morning blood sugar levels rose to 210 mg/dl and hyperglycemia symptoms (i.e., polyuria) resulted.

EXAMPLE 4

A male Caucasian, 17 years of age, 5'2" in height, 116 pounds having Type I diabetes mellitus diagnosed in November, 1995, one year before herbal treatment commenced, was very active and strenuously exercised daily, was on vitamin and mineral supplements since November, 1995 with minimal results. Beginning December, 1996, the subject ingested 375 milligrams of bilberry fruit and 530 milligrams of valerian root approximately thirty to forty-five minutes after each meal. After initial dosage, blood sugar level was 230 mg/dl in the p.m., and the morning after a.m. blood sugar level was 118 mg/dl.

The subject had commenced insulin in November, 1995 for two weeks, then was off insulin until July, 1996. Beginning in November, 1996, insulin intake varied between 3 and 4 regular, 11 and 12 NPH in the a.m., and one half to three regular, 5–6 NPH in the p.m. Subject altered insulin intake because of variation in exercise levels and frequency, and also because of weight and height gain during adolescence. As of July, 1997, subject was stable and regulated at an insulin intake of 7 regular, 16 NPH in the a.m., and 5 regular, 10 NPH in the p.m. Subject is in a "honeymoon" period where there is significant remaining insulin function.

The daily blood glucose average for May, 1997 was 131 mg/dl while the daily average for June, 1997 was 141 mg/dl. Glycosylated hemoglobin was 8 before insulin injections commenced and after six months of treatment the glycosylated hemoglobin level is 8.8.

Subject is on vitamin and mineral supplements, including vanadyl sulfate and chromium picolinate and gymnema sylvestre, which are known hypoglycemic agents.

Based upon the test results, the treatment for adult onset (Type II diabetes) requires ingestion of bilberry fruit (approximately 375 milligrams of the milled herb) and valerian root approximately 400 to (450 to 500 milligrams of the milled herb) within thirty to forty-five minutes after every meal. It is preferable that the ratio of bilberry to valerian root be approximately one to one. The range of maximum efficacy can be tailored to the subject. Meals should be confined to a diabetic diet, which restricts intake of refined carbohydrates (sugar, white flour products such as breads, cakes and sweets) saturated fats (animal fats as lamb and beef fat on meat, butter, cream, cheese, and whole milk and red meats (beef and lamb).

Herbal vitamin and mineral supplements must be taken with the meal and not with the bilberry fruit and valerian root. Timing is important. If the herbs are ingested more than forty-five minutes after a meal, they lose their efficacy.

If morning blood sugar is high, one bilberry fruit and one valerian root capsule should be taken before bedtime. Snacking after ingestion of bilberry and valerian root eliminates effectiveness in lowering blood sugar. Snacking on no-calorie foods is permissible, but carbohydrates and proteins must not be ingested after the bilberry and valerian root ingestion until the subject's next meal, unless the subject becomes hypoglycemic or has a tendency toward hypoglycemia.

It is preferable that the subject exercise at least one half hour a day. If a subject is on insulin and wishes to take bilberry and valerian, the subject may become hypoglycemic after the first couple of doses, and may need insulin reduction.

Possible side effects of ingestion of bilberry fruit and valerian root in timed relation to meals of a diabetic diet include (i) extreme hypoglycemia after initial and subsequent doses; (ii) valerian root sensitivity in subject with prior intestinal conditions such as diverticulitis, (iii) enhanced effectiveness of blood sugar reducers such as penicillin and its derivatives such as, amoxycillin, as well as mineral hypoglycemic agents as chromium picolinate and vanadyl sulfate, (iv) insulin dependent diabetes mellitus subjects will experience hyperglycemia especially in the early stages of treatment if the bilberry and valerian are discontinued or are not taken at the prescribed times, and (v) sensitivity to regular insulin.

I claim:

1. A method for lowering blood glucose levels in diabetic humans who are being maintained on a diabetic diet, the method comprising ingestion of a therapeutically effective amount of bilberry fruit and valerian root after each meal.

2. The method according to claim 1, wherein the ingestion of bilberry fruit and valerian root occurs approximately 30 to 45 minutes after each meal.

3. The method according to claim 2, wherein the bilberry fruit comprises approximately 375 milligrams of milled bilberry fruit, or an equivalent of concentrated extract of bilberry fruit.

4. The method according to claim 3, wherein the valerian root comprises between approximately 400 milligrams and approximately 530 milligrams of milled valerian root, or an equivalent of concentrated extract of valerian root.

\* \* \* \* \*